United States Patent
Talmore

[11] Patent Number: 5,344,433
[45] Date of Patent: Sep. 6, 1994

[54] APPARATUS FOR THE TREATMENT OF SKIN WOUNDS

[75] Inventor: Eli Talmore, 15/5 Eliezer Alter Street, Ramat Alon, Haifa, Israel

[73] Assignees: Dimotech Ltd.; Eli Talmore, Israel

[21] Appl. No.: 974,916

[22] Filed: Nov. 12, 1992

[30] Foreign Application Priority Data

Nov. 28, 1991 [IL] Israel .................................. 100181

[51] Int. Cl.$^5$ ................................................ A61N 5/06
[52] U.S. Cl. .................................................... 607/88
[58] Field of Search ............... 607/88, 90, 94; 604/53; 362/217; 128/6; 385/141; 315/39; 514/167; 250/504 R, 372; 364/413.26, 413.3

[56] References Cited

U.S. PATENT DOCUMENTS

| | | | |
|---|---|---|---|
| 3,911,318 | 10/1975 | Spero et al. ........................ | 315/39 |
| 4,048,537 | 9/1977 | Blaisdell et al. .................... | 362/217 |
| 4,298,005 | 11/1981 | Mutzhas ............................. | 607/94 |
| 4,428,050 | 1/1984 | Pellegrino et al. ............... | 364/413.26 |
| 4,558,700 | 12/1985 | Mutzhas . | |
| 4,686,986 | 8/1987 | Fenyo et al. ...................... | 607/90 |
| 4,712,014 | 12/1987 | Eich . | |
| 4,799,754 | 1/1989 | Goldenberg ......................... | 604/53 |
| 4,830,460 | 5/1989 | Goldenberg ......................... | 128/6 |
| 4,909,254 | 3/1990 | Wilkinson . | |
| 5,026,135 | 6/1991 | Booth .................................. | 385/141 |

*Primary Examiner*—Lee S. Cohen
*Assistant Examiner*—Brian M. Green
*Attorney, Agent, or Firm*—Morgan & Finnegan

[57] ABSTRACT

A method and apparatus for the treatment of psoriasis skin wounds are described. The method is based on the use of a short arc lamp having the capability of providing a narrow beam light source. The light source possesses a high intensity, the minimum irradiance applied being at least 1 mW/cm$^2$ to be obtained by a light guide. The light guide is made from fused glass or an anaerobic liquid, with a diameter in the range of 2 to 10 mm and provides a transmittance of above 70%. The apparatus using this method, comprises a lamp selected from Xenon or Mercury-Xenon type, a glass lens, a black filter and a light guide having a diameter in the range of between 2 to 10 mm. It can be connected to a microprocessor, which by monitoring the time of treatment, delivers the correct dose of light.

2 Claims, 1 Drawing Sheet

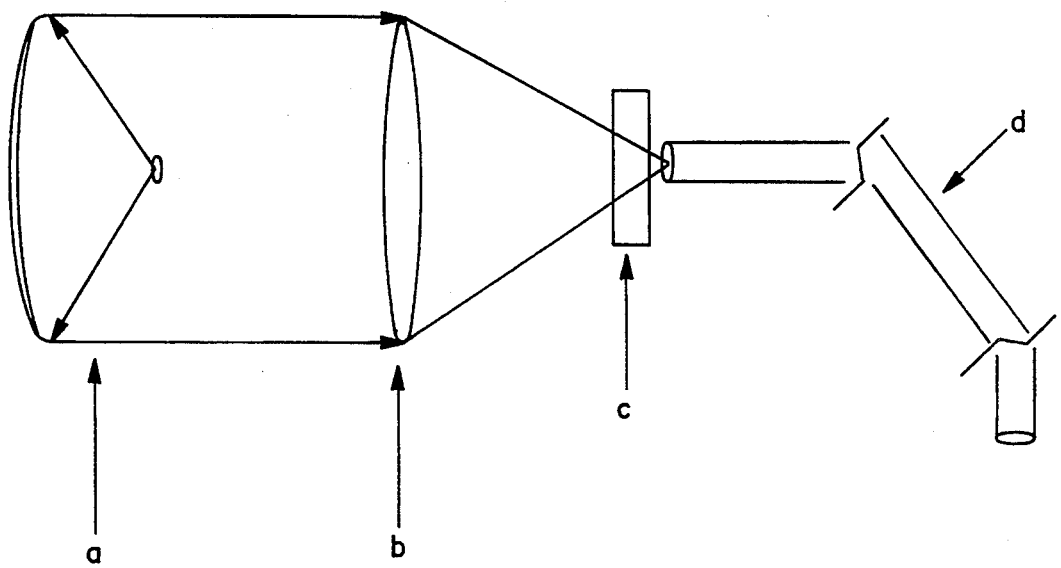

APPARATUS FOR THE TREATMENT OF SKIN WOUNDS

The present invention relates to a method and device for an efficient illumination of small areas with UVA radiation. More particularly, the invention relates to a method and device for the treatment of dermatological disorders.

BACKGROUND OF THE INVENTION

Psoriasis is a chronic skin disease caused by cell proliferation in the basal layer of the epidermis which results in severe physical and psychological effects. The disease is characterized by circumscribed red patches covered with white scales. Photochemotheraphy is considered as one of the most promising advances in dermatologic therapy in the last ten years.

Photochemotherapy combines the use of chemicals and electromagnetic radiation to treat various skin disorders. There are a large number of reports which show the effectiveness of treating psoriasis with a photosensitizing reagent Psoralen, which is orally administered or applied topically to the skin, and with ultraviolet radiation with a wave length range between 320 and 400 nm, a method also known as PUVA. The methoxypsoralen generally used as the reagent, is one of several naturally occurring photoactive furocoumarin compounds found in plants such as clove, dill, lemon, parsley, etc. and has been evaluated extensively for the chemotherapy of psoriasis.

As known, the ultraviolet spectrum is subdivided into three main regions:

UVA, considered as long wave, with a spectrum in the range of 320–400 nm;

UVB, considered a middle wave, with a spectrum in the range of 290–320 nm, known as a sunburn region; and UVC, considered a shortwave, with a spectrum in the range of 100–290 nm, known as a germicidal region.

Since metoxypsoralen reaches a maximum absorptive spectra at the wavelength of 325 nm, only the longwave ultraviolet light (UVA) was found to be useful as the light source. Also, UVA is less erythrogenic to normal skin than the UVB band, so that there is a lower risk of sunburn when UVA radiation is used. The methoxypsoralen serves also to make the skin more sensitive to the UVA radiation.

In contrast to the UVA treatment, known also as photochemotherapeutic method, there is the UVB treatment, known also as phototherapeutic method, in which only the therapeutic effects of UV radiation are used without the additional use of any chemical reagents. Generally, for this method the devices used as ultraviolet radiation are selected from light sources which contain UV emitting fluorescent lamps (a type of low pressure radiation devices), mercury high pressure radiation devices, Xenon radiation devices or mercury high pressure radiation devices doped with metal halides.

The shortwave radiation below 315 nm is suppressed by filters. There are known some UV fluorescent lamps in which the UV-B (under 320 nm) proportion is only a very low percentage whilst the UV-A proportion (over 320 nm) is very high. All the known devices are using suitable filters in order to suppress the undesired ultraviolet radiation. The literature is quite abundant with patents describing various devices with particular filters which are claiming to obtain the desired goal, i.e. a maximum UVA radiation to combat this disease.

Patients with severe psoriasis were faced with a choice between hospitalization and long-term ingestion of patent drugs that pose significant and potentially fatal complications. Accordingly, the approach of ambulatory psorlasis treatment became more and more considered as a most useful tool.

According to U.S. Pat. No. 4,712,014 the radiation lamp unit comprises a plurality of concave reflectors and light-orange radiation lamps and two UV lamp units which are arranged symmetrically to the center axis and in front to the focal point area of the light-orange radiation.

According to U.S. Pat. No. 4,558,700 a UVB device useful for phototherapy of psoriasis is described. The device is characterized by its capability to correlate the radiation dose to the erythema threshold dose as a function of the radiation intensity of the wave length range of the ultraviolet resulted from an edge filter. The edge filter is made from an organic material such as polymethylmethacrylate, polyethylene terephthalate or polyvinyl chloride.

According to a very recent U.S. Pat. No. 4,909,254 a method for the phototherapy of skin wounds is described, using ultraviolet light from which the UVB component is substantially removed so that the wound is irradiated with UVC—having a wavelength of 200 to 280 nm—and UVA. The device used, comprises a high-pressure mercury-vapor gas-discharge lamp with a quartz envelope and a special construction of a selective UV-filter. The UV-filter comprises at least 2 layers and preferably up to 21 layers of dielectric materials which are non-absorbing in the UV region and which have different refractive indexes. Among the suitable materials to be used as filters there are mentioned: hafnium oxide, magnesium oxide, ytrium oxide, aluminum oxide and silicon dioxide.

Among the disadvantages of the known devices used phototherapy there should be mentioned their robust construction and only a partial effect which they produce against psoriasis, as well as their carcinogenic effect.

It is an object of the present invention to provide a simple method to be used against psoriasis. It is another object of the present invention to provide a simple device to be used for the ambulatory psoriasis treatment.

It is yet another object of the present invention to provide a simple device which overcomes the disadvantages inherent with known photo-chemotherapy, whereby the other beneficial properties of UV radiation can be utilized without the unnecessary damages and carcinogenic problems inherent with UVB radiation which is substantially completely eliminated.

BRIEF DESCRIPTION OF THE INVENTION

The invention relates to a photochemotherapy method and apparatus for the treatment of psoriasis skin wounds using a short arc lamp having the capability of providing a narrow beam light source possessing a high intensity, being characterized that the irradiance applied is at least 1 mW per $cm^2$ being achieved by using a light guide. The light guide may consist either from a fiber optics bundle or an anaerobic liquid. The transmittance of the light guide is a function of the material from which it is made, its length and its wavelength. Thus for instance, a liquid light guide of half meter length, will transmit 70% of UVA radiation. The ability of the light guide to collect the incoming radiation is a function of its diameter and numerical aperture (N.A.). A most preferred irradiance to be applied is about 5mW per cm². It was found that using this method, the psoriasis is cured in a relatively short period of treatment, while the potentially dangerous UVA radiation is not applied on the healthy areas where its penetration depth is high.

Among the main advantages of the method the following can be mentioned:

The damaging UVB radiation, known by its carcinogenic effect, is completely eliminated.

The irradiation efficiency is much more effective than with other known devices, thus requiring a shorter time of exposure.

The irradiation is applied selectively onto the sick areas, while the healthy areas can be protected from potentially harmful radiation.

The resulting irradiance is much higher than that of the commonly used laser sources.

DESCRIPTION OF THE DRAWING

FIG. 1, is a schematic illustration of the apparatus according to a preferred embodiment of the present invention, wherein:

(a) is a lamp possessing a narrow beam light with a high intensity, provided with a fixed internal reflector which assists the obtaining of an increased intensity;

(b) is a glass lens, which has the role to focus the beam of the light. This lens, although being only optional, assists, to a certain extent, the complete removal of the residual radiation in the range of 300–330 nm emitted by the lamp;

(c) is a black interference filter which eliminates from the beam all the radiation above 370 nm. An alternative embodiment, pertaining the same function includes the combination of 45° dicroic mirror (UV-Vis transmitting and IR reflecting) and black glass absorption filter (visible absorbing). A most typical transmittance of this filter is around 0.5. This filtration is absolutely required in order to reduce the unnecessary power load, either visible or infra-red, on the subsequent guide light and to reduce the unwanted irradiation on the patient skin;

(d) is a light guide, generally made from fused silica or anaerobic liquid. Generally the diameter of the light guide is in the range of 2 to 10 mm and preferably around 5 mm when it accepts the radiation in the cone of 47° to 56°.

DESCRIPTION OF A PREFERRED EMBODIMENT

According to a preferred embodiment, the method will produce a complete curing of the psoriasis in a relatively short period of treatment, when the light guide provides a transmittance of 70%, The apparatus may also be further improved by connecting the apparatus as described above with a microprocessor, as a control unit, which enables a smooth and automatic operation. The microprocessor also controls the time exposure and program treatment as well as the number of treatments scheduled for a complete curing. Also it will be possible by monitoring the time of treatment, to deliver the correct dose of light, irrespective of the beam dimensions and independent of the loss of radiant output of the lamp with time.

A typical example of an apparatus according to the present invention, with the particular data of its components is hereinafter illustrated, with reference with the attached FIG. 1.

A rugged Xenon short arc lamp of 300 w power (a), which provides the narrow beam light, with an output of 1W and in the range of 330–370 nm was used as a source for the light, possessing a 1″ reflector aperture with a beam divergence of 10°, resulting in a throughput of 11.7 mm² sr. The light guide of 5 mm diameter and numerical aperture of 0.47 has a throughput of 14.3 mm² st. Therefore, all the energy collected by the lens (b) will be accepted by-the light guide.

The glass lens of type BK7 used (b), possessed a transmittance of 0.9 and the filter (c) has a transmittance of 0.5. The transmittance of the light guide was 0.7.

The beam emerging from the lamp, possesses certain spatial non-uniformity and its intensity decreases towards the edges of the beam. If the beam is focussed on the entrance edge of the light guide, then the output beam will have a very narrow angular divergence, similar to the laser beam. In some applications, a broad uniform beam, illuminating larger areas is required. In this case, the entrance of the light guide is moved towards the lense. This defocussing will result in a loss of the output energy, a typical loss being about 45%. The output beam is uniformly divergent, typical being a full angle of 50°. Based on the above data, the output energy (P) resulted from the light guide was:

$$P = 1000 \times 0.9 \times 0.5 \times 0.7 \times 0.55 = 173 \ mW$$

This energy was focussed on a skin area of about 10 cm². According to that, the irradiance obtained (E) will be:

$$E = \frac{173}{10} = 17.3 \ mW/cm^2$$

This irradiance is more than three times higher than the value of 5 mW/cm² expected to be obtained with a common device used in the PUVA treatment. In this manner, a corresponding significant reduction in the time of treatment will be involved (from 10 minutes to 3 minutes).

As appears from the above typical Example, the irradiation efficiency is much more effective then with existing devices, thus resulting in considerable shorter exposure times. The irradiation 1s applied selectively onto the sick areas, generally in the range of 1 to 10 cm², while healthy areas are protected from potentially harmful radiation.

The use of the apparatus according to the present invention, enables great flexibility in reaching remote and covered areas, such as scalp, under-arms, etc. This is a clear advantage of the apparatus according to the present invention. Furthermore, in contrast to the previous known radiation lamp units, the apparatus does provide a uniform treatment of the skin infected by psoriasis.

Although the invention has been described particularly for the treatment of psoriasis, it should be pointed out that one may conceive to use the method and apparatus also for other dermatological disorders such as: Mycosis fungoides, atopic eczema, lichen planus, ptyriasis lichenoides, uticaria, pigmentosa, polymorphous light eruption, alopecia areata, vitiligo, etc.

In addition to the skin wounds mentioned above, the device may be also applicable in the biological research for UVA molecular excitation, such as photo-affinitive labelling. Other applications may include blood sterilization, using psoralem binding to the virus followed by a subsequent irradiation with UVA light thus resulting in virus destruction.

Preliminary tests with the apparatus, indicate that skin wounds were healed more quickly than with other known devices.

An additional advantage of the apparatus is the fact that it can be considered ambulatory, due to its small dimensions and accordingly can be used on patients either at home or in their private office setting.

The foregoing describes only a most preferred embodiment of the apparatus according to the present invention and modifications obvious to those skilled in the art, can be made thereto without departing from the scope of the present invention, which is covered by the appended claims.

I claim:

1. An ambulatory apparatus for the treatment of psoriasis skin wounds which comprises:
    a lamp possessing a narrow beam light with a high intensity for emitting ultraviolet and infro-red rays to the skin to be treated;
    a glass lens which receives the rays, and focuses the beam of the light, said glass leans completely removing residual radiation in the range of 300 to 330 nm;
    a black filter for receiving and filtering said focused rays having a transmittance of about 0.5 in the UVA and substantially a zero transmittance from 370 nm up to 750 nm; and
    a liquid light guide having a diameter in the range of between 2 to 10 nm for receiving said filtered rays, and directing said filtered rays toward an area to be treated said liquid light guide providing at least 70% transmittance in UVA and substantially zero transmittance above 750 nm.

2. An apparatus according to claim 1, wherein said lamp is a Xenon or Mercury-Xenon type.

* * * * *